US008374455B2

(12) United States Patent
Allegre et al.

(10) Patent No.: US 8,374,455 B2
(45) Date of Patent: Feb. 12, 2013

(54) METHOD OF ANALYZING AN IMAGE OF HYDRIDES IN A METAL ALLOY, NOTABLY IN A NUCLEAR FUEL CLADDING ALLOY

(75) Inventors: Stéphane Allegre, Massy (FR); Loïc Sachot, Issy les Moulineaux (FR); Olivier Rabouille, Fontenay aux Roses (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 198 days.

(21) Appl. No.: 12/808,163

(22) PCT Filed: Dec. 12, 2008

(86) PCT No.: PCT/EP2008/067444
§ 371 (c)(1),
(2), (4) Date: Jan. 26, 2011

(87) PCT Pub. No.: WO2009/077459
PCT Pub. Date: Jun. 25, 2009

(65) Prior Publication Data
US 2011/0116680 A1 May 19, 2011

(30) Foreign Application Priority Data
Dec. 14, 2007 (FR) ...................................... 07 08742

(51) Int. Cl.
*G06K 9/44* (2006.01)
(52) U.S. Cl. ........................... 382/259; 149/87; 376/450
(58) Field of Classification Search ................... 149/87; 376/450; 382/259
See application file for complete search history.

(56) References Cited

PUBLICATIONS

Onozawa et al., 5.6 Improved Technique for Hydrogen Concentration Measurement in Fuel Claddings by Backscattered Electron Image Analysis (II), 2008, Japan Atomic Energy Ageny (JAEA) Conference 2008, pp. 325-332.*
Racine et al., Experimental Investigation of Strain, Damage and Failure of Hydrided Zirconium Alloys with Various Hydride Orientations,2005, 11th International Conference on Fracture, Torino, Italy, 6 total pages.*
Costa, Application of Image Processing to the Characterisation of Nanostructures,2004, Reviews on Advanced Materials Science: Advance Study Center Co. Ltd., vol. 6. No. 1, pp. 12-20.*
Arsene et al., Hydride Embrittlement and Irradiation Effects . . . and Boiling-Water Reactor (BWR) ZIRCALOY Cladding Tubes: Part I. Hydride Embrittlement in Stress-Relieved, Annealed, and Recrystalized ZIRCALOYs at 20 and 300 degrees, Mar. 2003, A Metallurgical and Materials Transactions, vol. 34, No. 3, pp. 553-566.*

(Continued)

*Primary Examiner* — Matthew Bella
*Assistant Examiner* — Dennis Rosario
(74) *Attorney, Agent, or Firm* — Baker Hostetler LLP

(57) ABSTRACT

The original image composed of pixels representing a sample of the alloy, the hydrides being represented by groupings of pixels (21), the method comprises steps of processing the image (1, 2, 3, 4, 5) to obtain the skeleton of the groupings of pixels (21') contained in the image, the skeletonization step (5) being followed by a step (6, 10) of analysis pertaining to the groupings thus skeletonised. The analysis step allows the determination of the hydrogen content as well as the morphological study of the hydrides so as to determine their danger.

16 Claims, 5 Drawing Sheets

PUBLICATIONS

J.H. Zhang, et al., "Quantification et Caracterisation des Hydrures de Zirconium dans le Zircaloy-4 par Analyse d'Image," Journal of Nuclear Materials 195 (1992) pp. 17-23 (with English abstract).

Aude Racine, "Influence de l'Orientation des Hydrures sur les Modes de Deformation, d'Endommagement et de Rupture du Zircaloy-4 Hydrure," These de l'Ecole Polytechnique, Sep. 23, 2005, pp. 53-78 (with English abstract).

Briand, et al., "Segmentation de Defauts dans des Images of Radiographies Industrielles," Revue Traitment du Signal, vol. 5, No. 4, 1998, pp. 291-303 (with English abstract).

Litorowicz, "Identification and Quantification of Cracks in Concrete by Optical Fluorescent Microscopy," Cement and Concrete Research, vol. 36, No. 8, pp. 1508-1515.

* cited by examiner

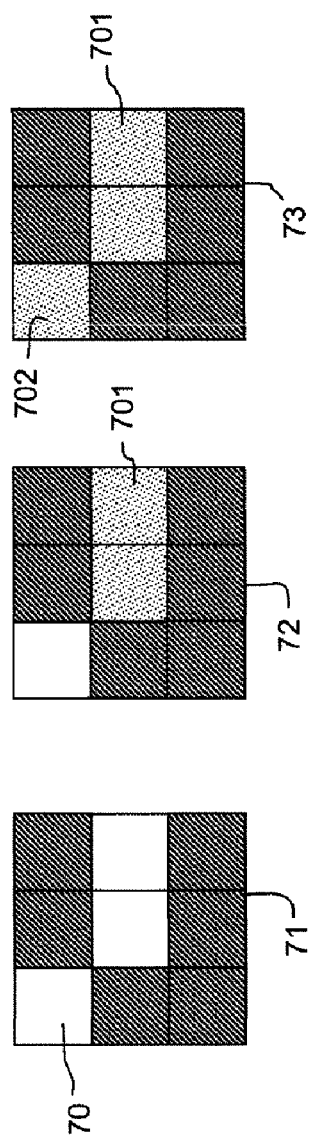
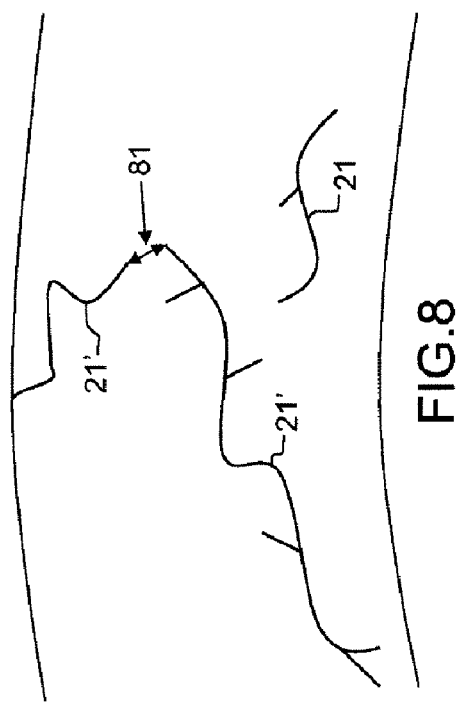
FIG.7
FIG.8

METHOD OF ANALYZING AN IMAGE OF
HYDRIDES IN A METAL ALLOY, NOTABLY
IN A NUCLEAR FUEL CLADDING ALLOY

CROSS-REFERENCE TO RELATED
APPLICATIONS

This application is a National Stage of International patent application PCT/EP2008/067444, filed on Dec. 12, 2008, which claims priority to foreign French patent application No. FR 07 08742, filed on Dec. 14, 2007, the disclosures of which are hereby incorporated by reference in their entirety.

FIELD OF THE INVENTION

The present invention relates to a method for analyzing an image of hydrides in a metal alloy. It applies notably to metallographic examination by image analysis, for example on alloys of zirconium, a material for cladding fuels used in nuclear power stations.

BACKGROUND OF THE INVENTION

Industrial inspection operations, notably for inspecting materials, use image analysis. This type of analysis is notably applied to the inspection and maintenance of the cladding for fuels of nuclear power stations, these claddings being made of zirconium. Because of the very low limit of solubility of hydrogen in zirconium at ambient temperature, it precipitates with the latter in the form of hydrides which may, in certain circumstances, be harmful for the mechanical strength of the claddings. The quantity of hydrides formed at ambient temperature is directly proportional to the hydrogen content in the material. The image analysis of a cladding sample can be used to quantify the hydrogen content shown by this sample, the image being obtained for example by optical microscopy or by electronic scanning microscopy. Other information relating to the morphology of hydrides, for example their mean size, their proximity or their orientation relative to a known axis is also quantifiable by image analysis.

This method has several advantages over the method of vacuum thermal extraction, because it is a localized and non-destructive analysis for hydrides, which is particularly important on irradiated materials. It is thus not necessary to destroy the samples in order to analyze them. One and the same sample may then undergo several examinations. Notably this makes it possible to make the analysis economically viable by avoiding using too many samples, in the case of awkward operations which require much handling.

However, during the preparation of the samples before images are taken, the latter undergo polishing and a chemical attack. The object of the chemical attack is to reveal the hydrides. The acid mixture preferably dissolves the hydrides which are revealed by optical contrast. Unfortunately, the chemical attack also slightly hollows out the matrix around the hydrides and tends to accentuate their size, particularly in thickness. Unlike an examination by electronic scanning microscopy, in backscattered electrons, where it is possible to observe the hydrides in their true dimension, in optical microscopy a hydride is wider the more virulent the chemical attack. It is therefore difficult to carry out a reliable analysis and notably an effective characterization of the hydrides.

SUMMARY OF THE INVENTION

The object of the invention is notably to allow a reliable analysis of hydrides from both the quantitative and qualitative point of view. Accordingly, the subject of the invention is a method for analyzing an image of hydrides in a metal alloy. The original image consists of pixels representing a sample of the alloy, the hydrides being represented by groups of pixels, said method comprises steps of processing of the image in order to obtain the skeleton of the groups of pixels contained in the image, the step of skeletonization being followed by an analysis step relating to the groups thus skeletonized, the analysis step executes a computation of the hydrogen content in the sample, the content being determined by the computation of an area H consisting of all of the groups of pixels of the image that are representative of the hydrides, said area H being compared with a calibration curve constructed on the basis of reference samples the hydrogen content of which is known, a group of pixels representative of a hydride matching predetermined measurement options, the calibration curve being a curve representative of the area H as a function of the hydrogen content, defined based on measurement points corresponding to the pairs formed by the area H and the corresponding hydrogen content of the reference samples, the computation of the area H being carried out in line with the same measurement options as for the sample to be analyzed.

The metal alloy is, for example, a zirconium alloy forming notably a protective cladding for nuclear fuel rods.

The area H is, for example, equal to the total of the areas of the groups of pixels representative of the hydrides over the total area of the image.

Advantageously, an analysis step delivers a danger factor of a hydride, this danger factor being a value that is a function of the morphology of the hydride in its skeletonized representation.

The danger factor of a hydride may be a function of its length L, of its orientation $\theta$ in the alloy or of its proximity, defined by a distance p from a closest hydride.

The danger factor of a hydride is for example a magnitude D defined according to the following relation:

$$D = \sqrt{L^2 + \theta^2 + \frac{1}{p^2}}$$

where L represents the length of the hydride, $\theta$ its orientation and p its proximity to the other hydrides.

Advantageously, a danger factor $D_{mean}$ is defined for the sample, this danger factor $D_{mean}$ being the mean of the danger factors of the hydrides present in the image of the sample.

Similarly, a maximum danger factor $D_{max}$ is, for example, defined for the sample, this danger factor $D_{max}$ corresponding to the maximum danger factor over all of the hydrides present in the image of the sample.

BRIEF DESCRIPTION OF THE DRAWINGS

Other features and advantages of the invention will become evident with the aid of the following description made with respect to appended drawings which represent:

FIG. 7, examples of rules of relatedness in order to define the belonging of pixels to one and the same hydride;

FIG. 8, an illustration of proximity between two hydrides.

DETAILED DESCRIPTION

Figure 1:
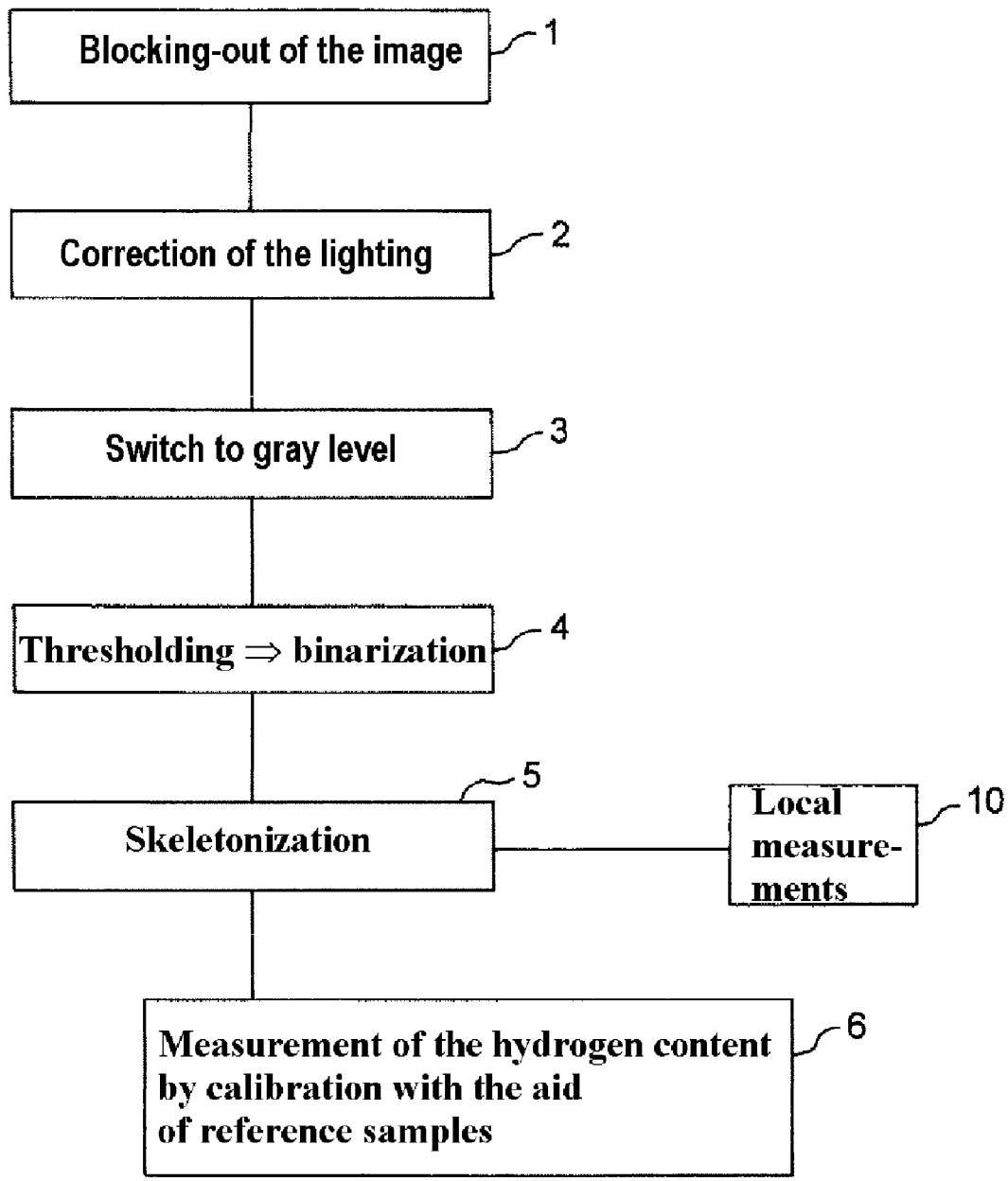
FIG. 1, an illustration of the possible steps of a method according to the invention.
Figure 2A:
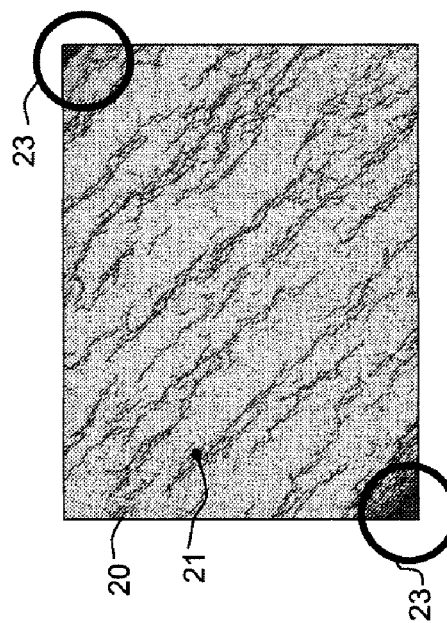
FIGS. 2a to 2d, illustrations of a first step of cutting the original image of an alloy sample.
Figure 2B:
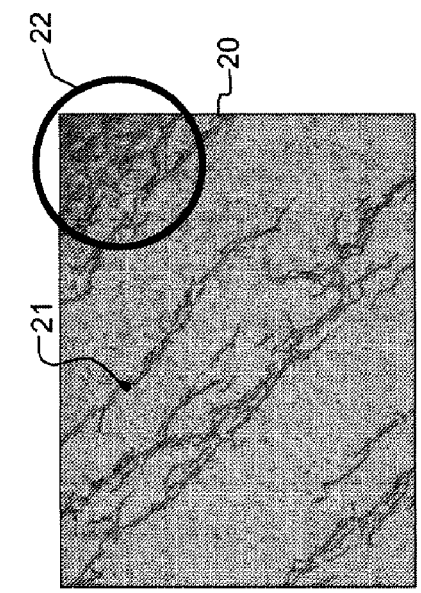

FIG. 1 illustrates the possible steps of a method according to the invention, applied, for example, to the analysis of the hydrides present in a zirconium alloy cladding of the fuel rods after irradiation in a nuclear power station. In a preliminary step, an image is taken of a sample of a cladding. This image is taken by optical microscopy or by any other means. FIG. 2*a* shows an example of an image obtained, comprising, for example, 760×570 pixels. This image 20 shows the traces of hydrides 21 present in the sample.

In a first step 1, the image is blocked out, and then in subsequent steps 2, 3, 4, 5, it is processed until an image of skeletic type is obtained, that is to say in which the traces of hydrides are reduced to the thickness of a pixel. Finally, in a last step 6, the hydrogen content is determined on the basis of the skeletonized image with the aid of reference samples via a calibration method.

FIGS. 2*a* to 2*d* illustrate the first step 1 of blocking out the image 20 for the purpose of obtaining notably an image of programmable dimensions, centered on the original image. This operation in particular makes it possible to eliminate the main problems associated with the effects of edges such as for example:

the blurred zones 22 on the edges, relative to the taking of the image;

the presence of pixels outside the cladding 23 at the edge of the image.

Figure 2C:
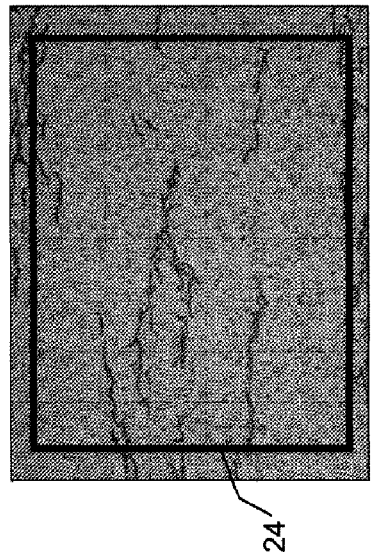
Figure 2D:
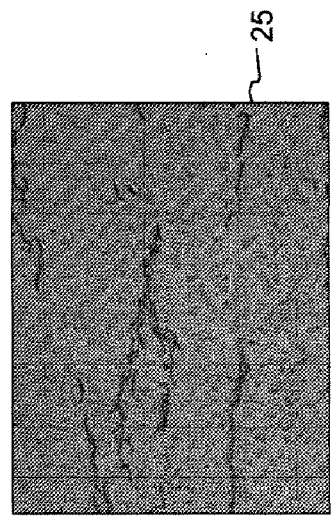

FIG. 2*c* illustrates the blocking-out 24 that is carried out giving the blocked-out image 25 of FIG. 2*d*. It is this image 25 that is subsequently processed.

The first step 1 can be followed by a step 2 of correcting the lighting of the blocked-out image 25. During the acquisition of images, the operator himself adjusts the intensity of the lighting. The lamps used usually perform variably over time and this also makes the lighting variable. The samples may also have a different reflective power. This second step 2 then makes it possible, if necessary, to reduce the lighting artifacts.

Figure 3:
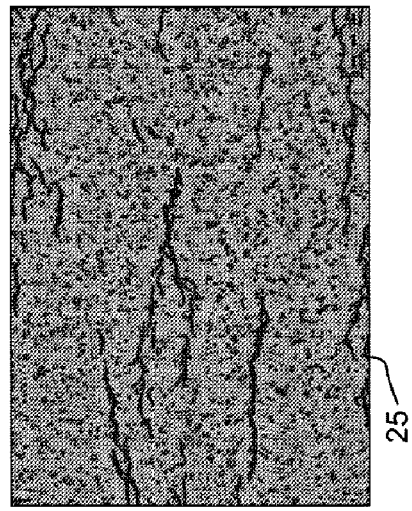
FIG. 3, an illustration of a step of binarization of the image.
Figure 3:
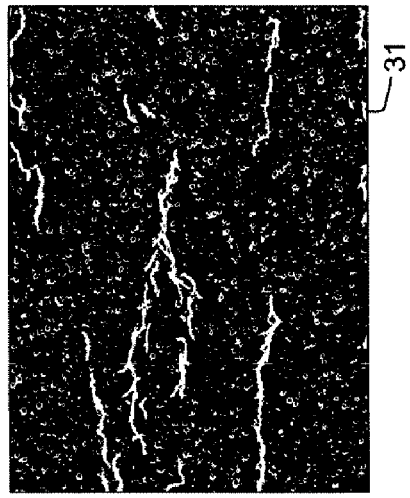

The next step 3 performs a switch of the colored image 25 to gray level. The switch to gray level means that a color image is not retained that may be too complex to carry out the thresholding of the next step 4. Several known solutions are possible for carrying out the switch to gray level. The image 25 of FIG. 3 is, for example, obtained according to the switch by intensity, the switch to gray level being carried out as a function of the light intensity. Other solutions are however possible.

FIG. 3 illustrates the next step 4 which carries out a thresholding followed by a binarization of the image. Several thresholding methods are known. The object of thresholding is to select the hydrides while taking only the minimum of undesired elements. Thresholding may be necessary for the analysis of an image. Specifically, the binarization of the image depends on this operation.

The binarization of the image follows the thresholding operation. Binarization consists in switching the image in gray level 25 to an image in black and white 31. This operation makes it possible to even further simplify the processing of the image for the purpose of selecting particles in this image.

Figure 4:
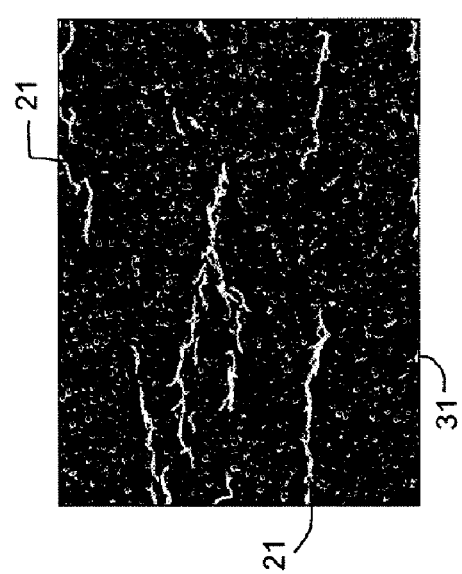
FIG. 4, an illustration of a step of skeletonization of the image.
Figure 4:
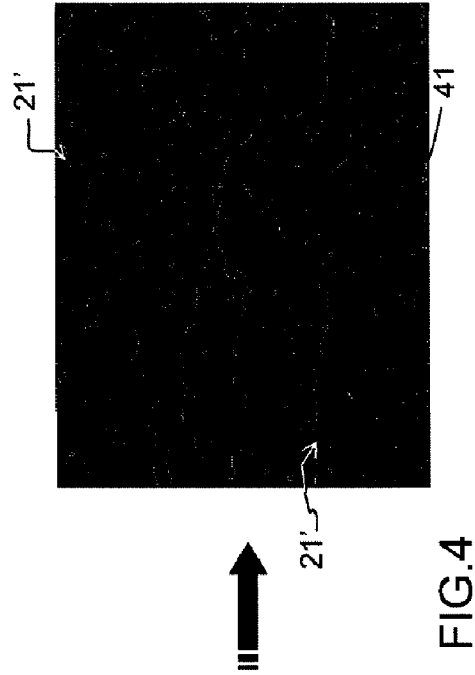

FIG. 4 illustrates the result obtained during the next step 5, called the skeletonization step. This operation is an ultimate erosion treatment of an object with a thickness of 1 pixel. FIG. 4 shows the image 31 before this skeletonization operation and the image 41 obtained. The hydrides 21 of the image 31 are then transformed into filaments 21' with a thickness of 1 pixel. The skeletonization mode used in the example of FIG. 4 is of the "light skeletonization" type. In this case, the skeletonization is carried out only on the pixels that are white on a black background, the white pixels corresponding to the hydrides. It is possible to use several degrees of skeletonization. The maximum degree transforms the hydrides into filaments that are one pixel thick. Lesser degrees of skeletonization may be used, and the hydrides are then transformed into filaments with thicknesses greater than 1 pixel, the final thickness depending on the degree.

Advantageously, the invention uses the fact that hydrides have, for a given material, substantially the same thickness irrespective of their concentration in the sample. The invention also uses the hypothesis that the hydrogen content of a zirconium alloy is directly proportional to the total length of the hydrides. This then makes it possible to assimilate a hydride to a filament without considering its thickness. The skeletonization step 5 makes it possible to obtain the filaments from which the content measurements will be carried out in the next step 6.

Figure 5:
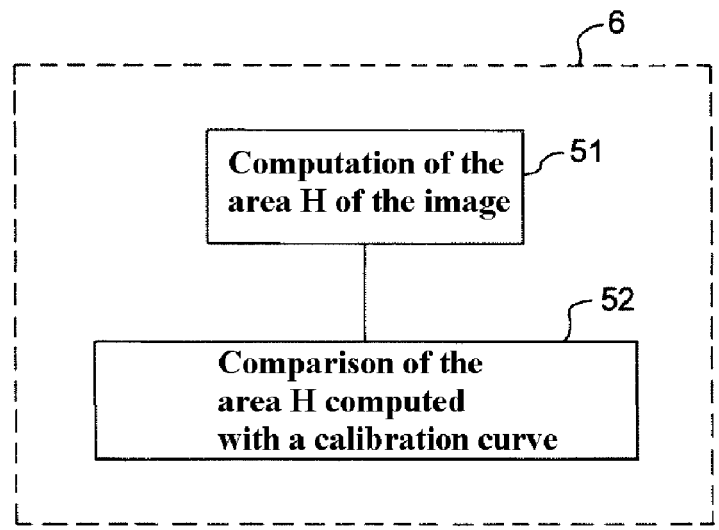
FIG. 5, an illustration of an analysis step giving the hydrogen content in the sample.

FIG. 5 shows the possible phases of this step 6 for measuring the hydrogen content. In a first phase 51, a magnitude characteristic of this content is computed, called the area H below. This magnitude takes account of the areas of the filaments corresponding to hydrides.

More particularly, it is a magnitude without dimension corresponding to the ratio of the total area of the detected hydride filaments over the total area of the skeletonized image 41. It is therefore defined by the following relation:

$$\text{Area } H = \frac{\sum \text{Areas of the detected hydride filaments}}{\text{Total area of the image}} \quad (1)$$

In practice, it can be defined by the following relation:

$$\text{Area } H = \frac{\sum \text{Area of the chosen white pixels}}{\text{Total area of the image}} \quad (2)$$

The chosen white pixels, corresponding to detected hydride filaments 21', depend on measurement options that will be defined below. Each area of the total $\Sigma$ is that of a group of pixels forming a particle. The measurement options define rules for choosing only the particles corresponding to hydride filaments.

In a second phase 52, the area H computed from the detected hydride filaments, according to the relation (2) for example, is compared with a calibration curve in order to obtain the hydrogen content in the sample.

Figure 6:
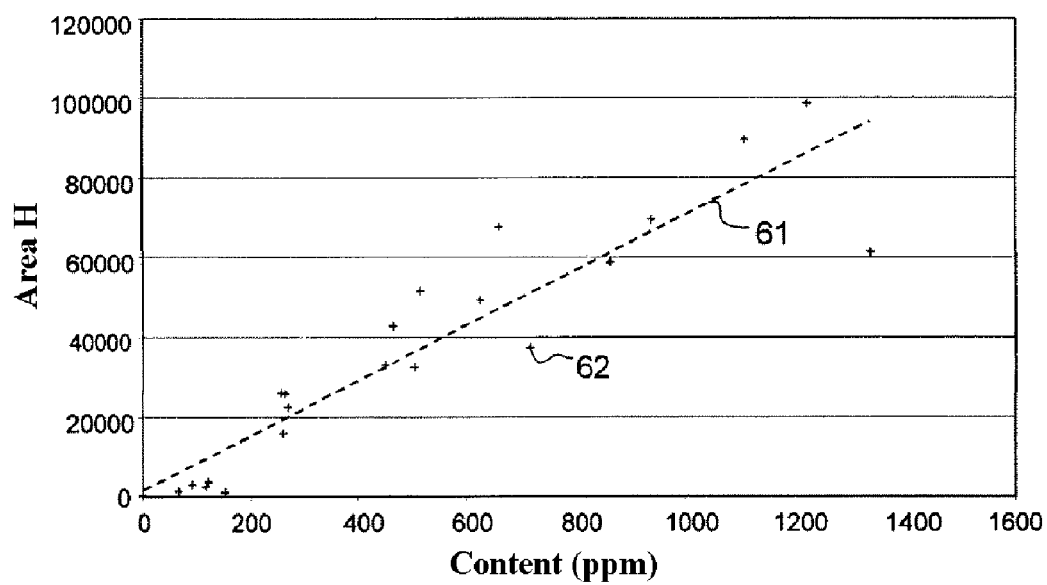
FIG. 6, an example of a calibration curve used to determine the hydrogen content.

FIG. 6 gives an example of a calibration curve 61. The Y axis represents the values of the area H and the X axis represents the hydrogen content, expressed in ppm.

This calibration curve is produced with the same measurement options as those cited above for the selection of the filaments. This calibration curve 61 is defined from measurements taken on reference samples showing an even distribution of the hydrides and of which the hydrogen content is known. For each of these samples, the area H is computed, according to the relation (2) for example, according to the same computing method as for the image 41 of the sample to be analyzed. For reasons of legibility, the area H computed according to the relation (2) is for example multiplied by $10^6$ so that its value varies between 0 and 120000 on the Y axis. The measurements taken on the reference samples are shown by crosses 62 in the system of axes of FIG. 6. For each reference sample, the user knows from first principles the hydrogen content marked on the X axis; the user computes its area H which he transfers to the Y axis to obtain the corresponding measurement point 62.

The calibration curve 61 is then for example a straight line the position of which is defined based on the position of the measurement points 62 of the reference samples. The straight line 61 is, for example, the straight line which shows the minimum distance relative to all of the measurement points 62. Once this calibration curve has been established, the hydrogen content contained in the image 41 of the sample to be analyzed is determined based on the computation of its area H. Based on the computed area H transferred to the Y axis, using the curve 61, the value of the corresponding X axis is determined which corresponds to the hydrogen content sought. The method is in this instance described manually with respect to a value computed on a Y axis. The curve 61 can of course be equated and the content obtained automatically by a computation based on the equation of the curve 61 and of the value of the area H of the sample to be analyzed.

This method of measuring the hydrogen content advantageously makes it possible to treat in totality a large number of images and perfectly meets the needs for quantifying the hydrides in materials.

To ensure that the method is fully reliable, it is necessary to provide a sufficient number of reference samples and therefore of measurement points 62. Any change to the measurement options also requires new sampling, that is to say the definition of a new calibration curve 61.

Several measurement options can be applied for the detection of the particles, that is to say of the groups of pixels. Notably, it is possible to choose the three options relative to the following parameters:
 the relatedness of the pixels in order to determine the belonging of pixels to one and the same particle;
 the minimum number of pixels in a particle in order to judge whether or not it is a hydride;
 the inclusions on the edges in order to determine whether the particles that have one or more pixels on the limits of the image 41 are or are not included in the measurement results.

With respect to relatedness, that is to say the number of adjacent pixels to take into account, it is a parameter which makes it possible to enlarge the particles. FIG. 7 illustrates two possible modes of selecting adjacent pixels based on an original square image extract 71 comprising 3×3=9 pixels including 3 white pixels 70.

The square 72 illustrates the selection option with four adjacent pixels. In this option, it is considered that two pixels of the same color 701 will form part of one and the same particle only if they are situated directly on adjacent pixels, that is to say above or below, to the right or to the left, as illustrated by the two original white pixels 701 that have been grayed out in the square 72.

The square 73 illustrates the selection option with 8 adjacent pixels. In this option, the field of detection is widened, that is to say that, from now onwards, the adjacent pixels on the diagonal 702 are considered to form part of one and the same particle. The original white pixels of the square 70, grayed out 701, 702 in the square 73, therefore form part of one and the same particle.

Once the rule for the belonging of pixels to one and the same particle is determined, it is necessary to define a minimum number of pixels that a particle must comprise to correspond to a hydride. It is possible, for example, to take this minimum number to be equal to 10 and thus eliminate all the particles smaller than 10 pixels. This filtering notably makes it possible to eliminate the majority of pinholes due to the preparation of the samples. Specifically, because of the skeletonization, the pinholes have been reduced to single particles or small size particles. When the skeletonization of an elongated shape, like a hydride for example, is produced, a filament is obtained with a thickness equal to 1 pixel. If the same operation is carried out on a rounded shape like a pinhole for example, either a short rounded shape with a thickness equal to 1 pixel or a single isolated pixel is obtained. Therefore, by skeletonization, followed by this filtering, it is possible to eliminate the defects due to the pinholes or to dust for example.

Finally, the options relating to the inclusions on the edges make it possible to determine whether the particles having one or more pixels on the edges must be taken into account for the measurements. Two options are possible. In a first option, the particles touching the edges are included in the measurements. This option is notably useful for computing the hydride content in an image. In a second option, the particles touching the edges are excluded from the measurements. This option may be chosen in the event of determining the mean length of the hydrides for example.

The measurement of the hydrogen content in a sample, a gross quantitative value without dimension, can be advantageously supplemented by local qualitative measurements of the hydrides in their context. These measurements are always taken from the skeletonized image 41. Specifically, the danger implied by the hydrides depends notably on their morphologies, also including their proximity and their orientations, particularly with respect to the possible propagation of a crack.

Returning to FIG. 1, it shows that, at the end of the skeletonization step 5, it is possible also to carry out, in another analysis step 10, local measurements, these measurements being for example the aforementioned qualitative measurements, that is to say the length of the hydrides, the orientation of the hydrides and their proximity corresponding to the distance between nearest neighbors.

The index of length of a hydride is important when it is a question of characterizing its danger for the material. Specifically, the longer a hydride is, the more a crack can run a long way in this hydride provided that its orientation is favorable with respect to the stress applied to the material. In the cladding of fuel, the radial orientation of the hydrides is the most critical with respect to fragility while circumferential orientation is favorable to good behavior of the material. Several criteria of length may thus be defined. It is of course possible to find the greatest length of the hydride if, for example, radial hydrides are involved. But in the case of mixed or mainly circumferential hydrides, it may be more useful to define the maximum length which can be traveled in the radial direction by a hydride.

Several solutions are possible for determining the length. In a solution that is simple to apply, for each particle, the highest and the lowest points on the vertical axis of the photograph corresponding to the radial axis are taken. Then the difference is calculated between the two ordinates which gives the radial length of the hydrides. This length is important to consider because it makes it possible to characterize, in the event of propagation of the crack, the distance that it can easily travel in the radial direction of the cladding. In the case of a radially-oriented hydride, this distance may be great. In the case of a circumferential hydride, this distance is zero or very small. Another measurement of the length of a hydride consists in finding the two furthest points in the hydride and in measuring the distance separating them, this distance then being considered to be the length of the hydride. Finally, it is always possible to define the length of a hydride as the total of the lengths of its fragmentations or branches.

The orientation index is also an important parameter in the local analysis in order to characterize the danger of the hydrides. Specifically, if it is accepted that the hydride is more fragile than the matrix, a radial orientation of the hydrides is then favorable to the propagation of a crack that may lead to a rupture of the cladding. It is therefore important to characterize the orientation of the hydrides in order to be able to determine their danger. In a skeletonized image 41 like that of FIG. 4, a hydride is a very ramified filament and the mean orientation of a hydride is not always the wisest parameter for characterizing its danger. It is therefore necessary to develop different parameters for measuring orientation that are representative of a risk and adapted to the particular morphology of the hydrides.

Several definitions of the orientation of a hydride may be used. In a first solution, a mean orientation $\theta_{mean}$ is defined according to the following relation:

$$\theta_{mean} = \frac{\sum_i \theta_i d_i}{\sum_i d_i} \quad (3)$$

where i represents the rank of a fragmentation of the hydride, $\theta_i$ represents the orientation of the fragmentation of rank i relative to a reference axis and $d_i$ represents the length of the fragmentation of rank i.

This gives a mean value of the orientation which is in relation with the lengths of the associated fragmentations. This definition of the orientation may be useful if it is desired to see the scattering of the orientation value because of the various ramifications.

In another definition of the angle of orientation, the two most distant points of each particle are taken. Then the orientation between these two points is computed, which is taken to be the orientation of the particle. In another definition, instead of considering the two most distant points, the orientation between the two most distant intersections is taken.

The index of proximity represents the degree to which the hydrides come together in a certain propagation direction. This means that, if a hydride A is considered, what is characterized is the fact that, in the event of propagation of a crack, the latter may or may not be easily propagated towards a hydride B when it reaches one end of the hydride A. The shorter the distance between the ends of the hydride A and those of the hydride B, the easier it is for a crack to pass from one to the other. The arrangement of the hydrides must be taken into account because two hydrides that are adjacent, parallel, radial and of the same length are not reliable situations for characterizing proximity. The case of two hydrides in line with one another is a critical case in a context of proximity. Several approaches are however possible. It is possible to consider that the cracks are propagated in a purely radial manner in a non-hydride-forming material. It is also possible to consider that the cracks are propagated at ±45° relative to the radial axis, which is a shearing phenomenon. A third approach proposes that the crack travels in the matrix along the orientation of the last portion of hydride that it has passed through.

Several solutions are possible for defining the proximity between two particles. FIG. 8 illustrates an example in which the proximity is defined by the distance 81 between the ends of the hydrides, represented by the filaments 21', that are the nearest neighbors. In order to determine this distance, the distance is computed, for example, between each end of one hydride 21' and the ends of the other hydrides 21', at an angle of between 0° and 180°, that is to say in the continuity of the tested hydride. For each end of a hydride, the minimum of this distance is taken if the orientation criterion has been validated. The proximity value p is the minimum of these minimum distances. Another, two-way method is possible. The process is the same as above except that a double passage is executed, on the one hand between 0° and 180° and on the other hand between 180° and 360°. This gives two distances. The chosen proximity value can be the mean of these two distances. Instead of taking the mean of the two distances, it is also possible to take the minimum of these two distances.

According to the invention, for each hydride represented by a filament 21', the user defines a magnitude D which characterizes the danger locally, in the more global environment of a fuel cladding for example. This danger factor D takes account of the length L of the hydride, its angle of orientation $\theta$ and its proximity p to another hydride. These parameters L, $\theta$ and p are, for example, defined according to the methods described above. The magnitude D is defined for example by the following relation:

$$D = \sqrt{L^2 + \theta^2 + \frac{1}{p^2}} \quad (4)$$

L and p are, for example, defined in μm and $\theta$ in degrees.

A mean danger factor $D_{mean}$ can be defined for all the hydrides of the image, this danger factor being, for example, the mean of the danger factors of all the hydrides. It is also possible to define a maximum danger factor $D_{max}$ corresponding to the maximum danger factor over all of the hydrides of the image.

The maximum danger factor advantageously makes it possible to know the most dangerous hydride for each image. The mean danger factor of the images makes it possible to compare these images with one another and therefore the materials with one another.

The invention has been described for application to a zirconium alloy; it can be applied to the analysis of hydrides in other types of alloy.

The invention claimed is:
1. A method for analyzing an image of hydrides in a metal alloy, the original image comprising pixels representing a sample of the alloy, wherein the hydrides are represented by groups of pixels, said method comprising steps of processing of the image in order to obtain the skeleton of the groups of pixels contained in the image, the skeletonization step being followed by an analysis step relating to the groups thus skeletonized, the analysis step executes a computation of the hydrogen content in the sample, an analysis step delivering a danger factor of a hydride, this danger factor being a value that is a function of the morphology of the hydride in its skeletonized representation, the danger factor of a hydride being a magnitude D defined according to the following relation:

$$D = \sqrt{L^2 + \theta^2 + \frac{1}{p^2}},$$

where L represents the length of the hydride, θ its orientation and p its proximity to the other hydrides.

2. The method as claimed in claim 1, wherein metal alloy is a zirconium alloy.

3. The method as claimed in claim 1, wherein the metal alloy forms a protective cladding of nuclear fuel rods.

4. The method as claimed in claim 1, wherein the area H is equal to the total of the areas of the groups of pixels representative of the hydrides over the total area of the image.

5. The method as claimed in claim 1, wherein the calibration curve shows the minimum distance from all of the measurement points of the reference samples.

6. The method as claimed in claim 1, wherein the length L of the hydride is defined by the total of the lengths of the branches of its skeletonized representation.

7. The method as claimed in claim 1, wherein the length L of the hydride is defined by the distance between the two most distant points of its skeletonized representation parallel to an axis.

8. The method as claimed in claim 1, wherein the length L of the hydride is defined by the distance between the two most distant points of its skeletonized representation.

9. The method as claimed in claim 1, wherein the orientation is defined by a mean orientation $\theta_{mean}$ according to the following relation:

$$\theta_{mean} = \frac{\sum_i \theta_i d_i}{\sum_i d_i}$$

where i represents the rank of the branch of the hydride, $\theta_i$ represents the orientation of the fragmentation of rank i relative to a reference axis and $d_i$ represents the length of the fragmentation of rank i.

10. The method as claimed in claim 1, wherein the orientation is the orientation between the two most distant points of the hydride.

11. The method as claimed in claim 1, wherein the orientation is the orientation between the two most distant intersections of branches of the hydride.

12. The method as claimed in claim 1, wherein a danger factor $D_{mean}$ is defined for the sample, this danger factor $D_{mean}$ being the mean of the danger factors of the hydrides present in the image of the sample.

13. The method as claimed in claim 1, wherein a maximum danger factor $D_{max}$ is defined for the sample, this danger factor $D_{max}$ corresponding to the maximum danger factor over all of the hydrides present in the image of the sample.

14. The method as claimed in claim 1, wherein the content is determined by the computation of an area H including all of the groups of pixels of the image that are representative of the hydrides, said area H being compared with a calibration curve constructed based on reference samples the hydrogen content of which is known, a group of pixels representative of a hydride matching options of measurements, the calibration curve being a curve representative of the area H as a function of the hydrogen content, the calibration curve being defined based on measurement points corresponding to the pairs formed by the area H and on the corresponding hydrogen content of the reference samples, the computation of the area H being carried out in line with the same measurement options as for the sample to be analyzed.

15. The method as claimed in claim 1, wherein the proximity p being defined by the distance between the proximity of the closest adjacent hydrides, this distance being defined by the computation of the distance between each end of one hydride and the ends of the other hydrides at an angle of between 0° and 180°, for each end the minimum of this distance is taken, the value of the proximity being the minimum of the minimum distances.

16. The method as claimed in claim 15, wherein the computation of the distance between each end of one hydride and the ends of the other hydrides at an angle of between 0° and 180° on the one hand, and between 180° and 360° on the other hand.

* * * * *

UNITED STATES PATENT AND TRADEMARK OFFICE
CERTIFICATE OF CORRECTION

PATENT NO. : 8,374,455 B2  Page 1 of 1
APPLICATION NO. : 12/808163
DATED : February 12, 2013
INVENTOR(S) : Allegre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 423 days.

Signed and Sealed this
First Day of September, 2015

Michelle K. Lee
*Director of the United States Patent and Trademark Office*